(12) United States Patent
Chege

(10) Patent No.: US 6,319,951 B1
(45) Date of Patent: Nov. 20, 2001

(54) USE OF 3-AMINO-4-HYDROXYBENZOIC ACID FOR THE TREATMENT OF RETROVIRAL INFECTIONS

(76) Inventor: Joseph Chege, P.O. Box 678, Gatundu (KE)

( * ) Notice: Subject to any disclaimer, the term of this patent is extended or adjusted under 35 U.S.C. 154(b) by 0 days.

(21) Appl. No.: 09/117,890

(22) PCT Filed: Feb. 5, 1997

(86) PCT No.: PCT/KE97/00005

§ 371 Date: Mar. 23, 1999

§ 102(e) Date: Mar. 23, 1999

(87) PCT Pub. No.: WO97/28795

PCT Pub. Date: Aug. 14, 1997

(30) Foreign Application Priority Data

Feb. 7, 1996 (GB) .................................... 9602444

(51) Int. Cl.[7] .................. A61K 31/125; A61K 31/34; A61K 31/70
(52) U.S. Cl. ..................... 514/567; 514/474; 514/52
(58) Field of Search .................. 514/567, 474, 514/52

(56) References Cited

FOREIGN PATENT DOCUMENTS

| | | | |
|---|---|---|---|
| 0 474 874 A1 | * 3/1992 | (EP) | ............ A61K/31/195 |
| 0474847 | 3/1992 | (EP) | ............ A61K/31/195 |
| 50-126814A | 10/1975 | (JP) . | |

OTHER PUBLICATIONS

Lancet, "Inactivation of HIV by Nonoxynol–9", 2, p. 645 (1988).
Lancet, "Liver Disease and Bileduct Abnormalities in Adults with Cystic Fibrosis", 2, pp. 1422–1425 (1989).
Medicine Digest, "Nonoxynol–9 and HIV", 14, No. 9, p. 58 (1988).
P.A. Gains, The Lancet, "Cholesterol Embolisation After Angiography," Mar. 19, 1988, p. 643.
A.Pompidou et al., The Lancet, "Inactivation of HTLV–III/LAV–Infected Cultures of Normal Human Lymphocytes by Nonoxynol–9 in Vitro," Dec. 21, 1985, pp. 1422–1423.
Medicine Digest, vol. 12, No. 4, Apr. 1986, p. 41.
The Lancet, 1:643, 1988.*
Harakeh et al 113CA:184287e, 1990.*

* cited by examiner

*Primary Examiner*—Russell Travers
(74) *Attorney, Agent, or Firm*—Morgan, Lewis & Bockius LLP

(57) ABSTRACT

3-amino-4-hydroxybenzoic acid or a derivative thereof is used in the preparation of a medicament for treating retroviral infections and HIV in particular. The 3-amino-4-hydroxybenzoic acid or a derivative thereof is also included in a pharmaceutical composition in combination with a pharmaceutically acceptable carrier and any of vitamin $B_{12}$, folic acid, vitamin C or a combination of two or more thereof.

9 Claims, 2 Drawing Sheets

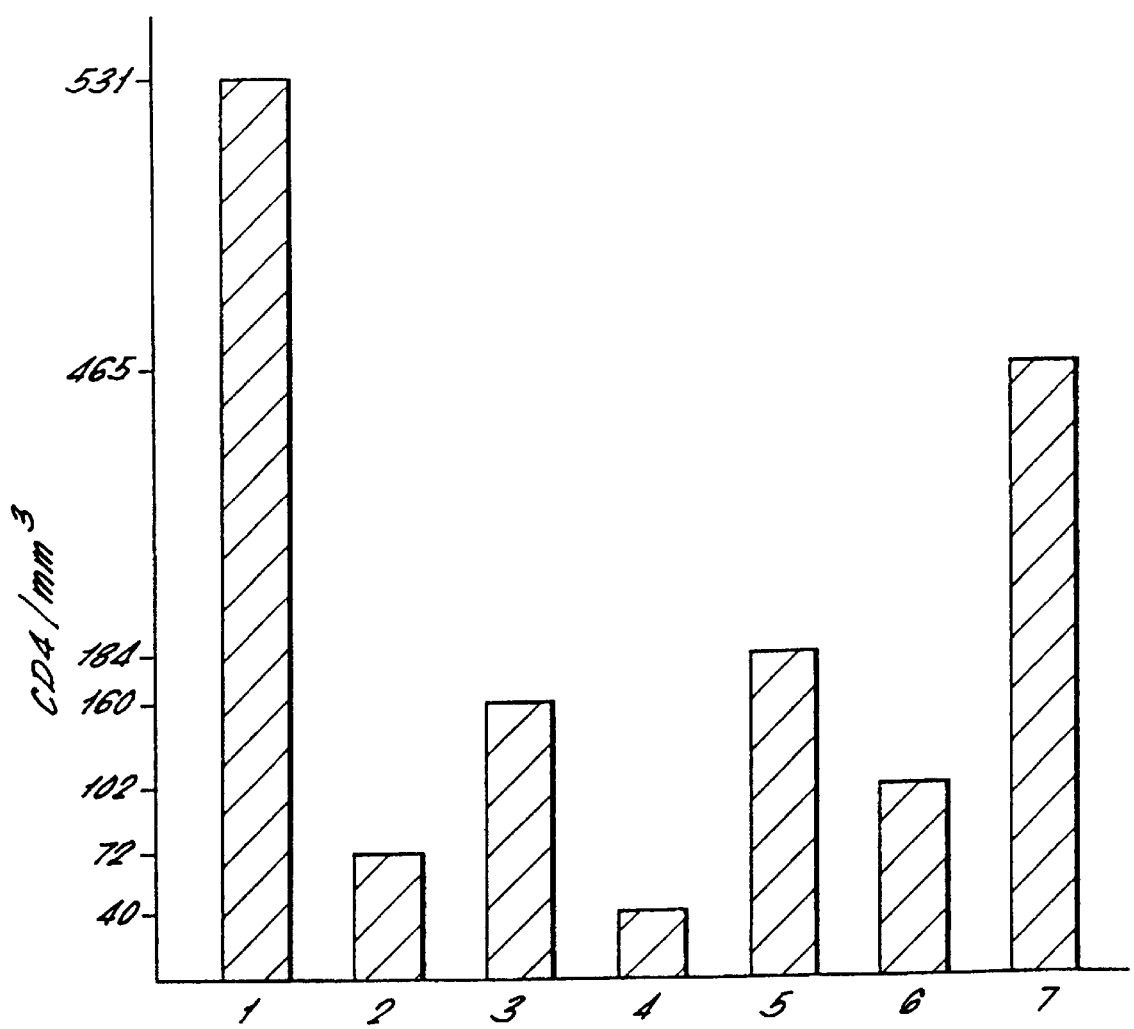

USE OF 3-AMINO-4-HYDROXYBENZOIC ACID FOR THE TREATMENT OF RETROVIRAL INFECTIONS

Figure 1:
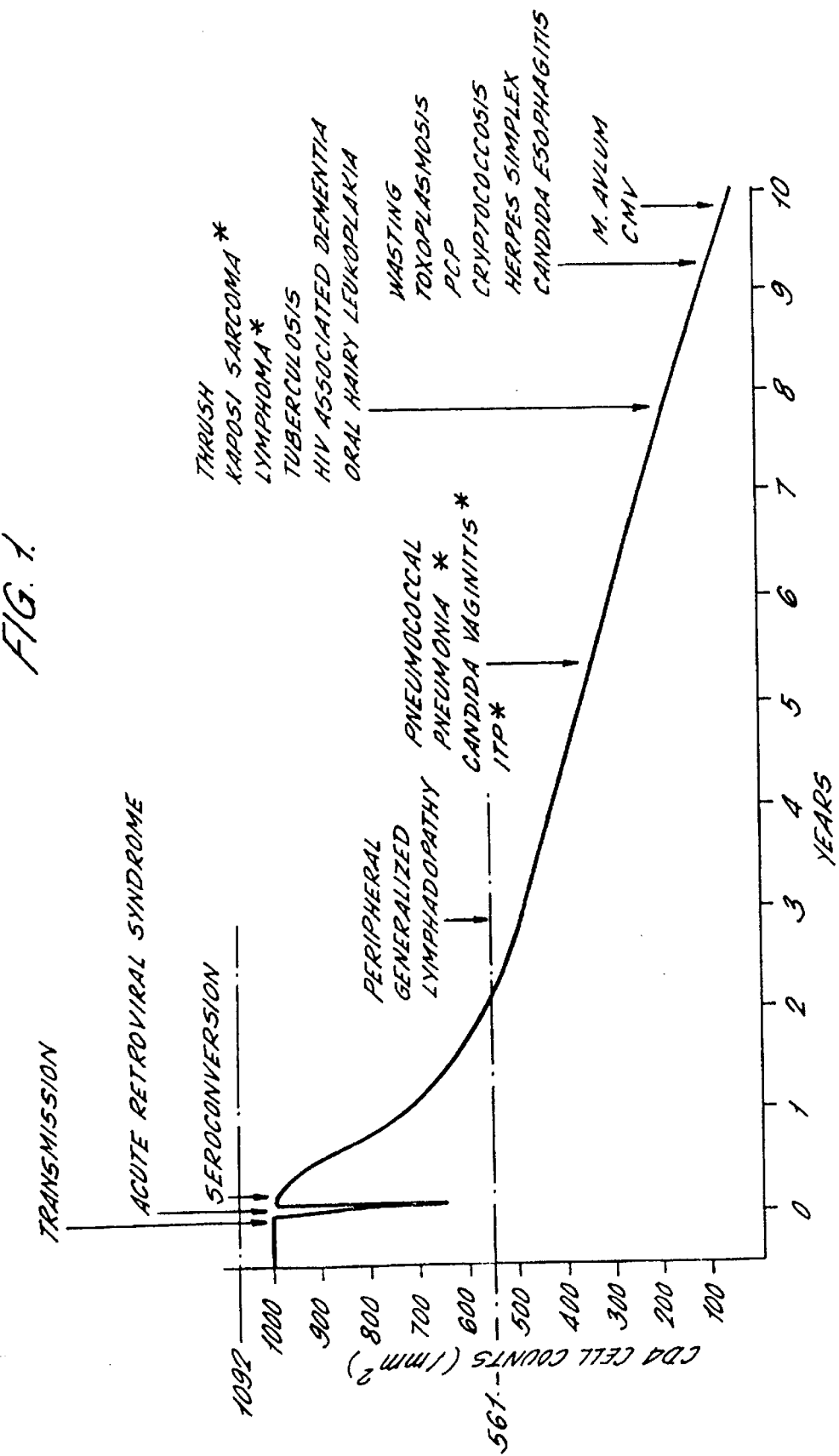

This application is a 371 application of PCT/KE97/00005 filed Feb. 5, 1997 which claims priority from United Kingdom Patent Application 9602444.3 filed Feb. 7, 1996.

The invention relates to use of 3-amino-4-hydroxybenzoic acid or a derivative thereof in the preparation of a medicament for treating viral infections and pharmaceutical compositions containing 3-amino-4-hydroxybenzoic acid or a derivative thereof. More specifically the invention relates to use of 3-amino-4-hydroxybenzoic acid or a derivative thereof in the preparation of a medicament for the treatment of retroviral infections, specifically but not exclusively HIV infection.

Acquired Immune Deficiency Syndrome (AIDS) is a disease complex caused by the Human Immunodeficiency Virus (HIV) which was identified for the first time in medical history in 1981. The causative virus was identified in 1983. It belongs to a group of RNA viruses called retroviruses.

Retroviruses were discovered in 1940. Later, Jarret discovered a retrovirus that causes Leukemia and immune deficiency in domestic cats. In 1970 Temin and Baltimore independently discovered the enzyme reverse transcriptase which allows transcription of RNA to DNA. From there the search for human retroviruses started leading to the discovery of HTLV-I (1979), HTLV-II (1982) and HTLV-III, the taxonomic equivalent of HIV (Dr Robert Gallo). HTLV-I immortalizes human cells leading to T-cell leukemia and a myelopathy called Tropical Spastic Paraparesis. HTLV-II does not cause any known disease. HTLV-III (HIV) exists as, HIV-1 and HIV-2 both of which cause human immunodeficiency. Simian Immuno deficiency Virus (SIV) also exists which causes a similar immune deficiency in monkeys.

The HIV enters the body in three main ways:
(a) mother/child—vertical transmission occurs before birth through breaches of the placenta or an infected gametocyte (sperm or ovum), at birth (connatal transmission), through breast feeding if there are cracks in the infant's buccal mucosa (postnatal transmission);
(b) through transfusion of infected blood or blood products; and
(c) through sexual contact, especially if there are venereal ulcers on the genitals. Apart from vertical transmission, all the other modes are referred to as horizontal transmission.

Once in the blood the HIV invades the following $CD_4$+ve cells by attachment, adsorption, adhesion and penetration:
(i) $CD_4$ lymphocytes
(ii) Monocytes
(iii) Macrophages
(iv) Follicular cells of lymph nodes
(v) Dendritic cells of the gastrointestinal tract, (GIT) and genito-urinary tract (GUT)
(vi) Langerhan cells of the skin
(vii) Microglial cells of the CNS
(viii) Multinucleated giant cells of the CNS Other cells which support HIV replication and which have no $CD_4$ markers comprise: Neurons, glial cells, B-lymphocytes, colo-rectal epithelial cells and myeloid precursor cells of the bone marrow. Affection of these cells seems to suggest the existence of other than $CD_4$ surface markers.

1. After entering the host cell the HIV single RNA chain replicates to form others. At some point it doubles to form DNA which attaches to the host DNA to form provirus which makes the viral infection "permanent" as long as that host cell lives.

The relationship established by a virus with its host may be:
(1) Symbiotic—as for provirus and herpes viruses
(2) Cytopathic—killing the host cell
(3) Hypertrophic—lytic, forms rashes which then burst after reaching a critical size and being secondarily infected by bacteria.
(4) Oncogenic—cancerous, as in leukemia Treatment of the viral infection depends on which of the above relationships the treatment is directed at.

The HIV exploits the host biochemistry to make viral RNA and DNA and paralyses the host biochemistry by secreting translational inhibitory protein (TPI). A cell so affected is incapable of enzyme, hormone and ATP formation. Lack of ATP energy leads to failure to maintain active transport for glucose, amino acids, other metabolites and wastes. Maintenance of the Gibbs-Donnan equilibrium to regulate electrolytes also fails. All these failures plus the lytic effect of viral enzymes on the host cellular membrane cause cell death.

These cytopathic effects are greatest on $CD_4$ lymphocytes because they have the surface markers for the HIV attachment and entry and they actively hunt for HIV, so enhancing contact. These lymphocytes are the principal controllers of both the cell-mediated and humoral types of immunity. When they are decimated the body immunity declines and the body succumbs to opportunistic infections (O.Is) from viruses, fungi, bacteria and protozoa. Opportunistic infections are so called because the healthy body can live within a symbiotic equilibrium with the causative organisms. The organisms take advantage of the low immunity to become pathogenic which they normally are not.

Attack by opportunistic infections is the hallmark of HIV/AIDS. The natural progression of $CD_4$s is used to assess prognosis and the progression of HIV/AIDS. The lower the count the more advanced the disease and the worse the prognosis. FIG. 1 shows a graph of the natural decrease of $CD_4$s in HIV/AIDS. The $CD_4$ count goes down by 30–50/mm$^3$ year. The point on the graph of a patient's CD count can be used to roughly indicate how long he has had the virus and indicate his prognosis.

Treatment according to the present invention raises the $CD_4$ count and reverses the progression of the curve to the left.

The infection can be confirmed by testing antibodies to HIV by ELISA or Western blot tests which will be positive at 2–4 weeks after infection. Children may harbour passive maternal antibodies which means that they may not have the HIV for up to 18 months after birth, although they will test positive.

Treatment of HIV/AIDS should be given at any stage after the presence of the HIV has been identified. It is advantageous that any HIV is killed early, before any opportunistic infection sets in. Accordingly, early screening is recommended.

Synthesis of RNA and DNA by the virus using the host biochemistry consumes a lot of vitamin $B_{12}$, folic acid and vitamin C. Depletion of $B_{12}$ has been found to be a uniform finding in all AIDS cases.

Medicaments for the prevention and/or treatment of HIV/AIDS, to date, are limited. HIV infection inverts the $CD_4$:$CD_8$ ratio. This inversion is permanent. There is no drug known to revert it back to normal, except the drug of this invention.

To qualify as an anti-HIV drug, a substance must fulfil one, two or all of the following:
(i) Be able to boost the patient's immunity.
(ii) Be able to halt the multiplication of the HIV in the body
(iii) Be able to eliminate the HIV from the patient's body The compound 3-amino-4-hydroxybenzoic acid has the chemical formula $C_7H_7NO_3$ and the structural formula:

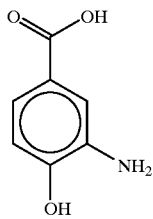

It is a white powder, not readily soluble in water.

The compound has previously been used orally as a Maillard reaction inhibitor as disclosed in European Patent 0474874 for treatment of diabetes mellitus. It has also been used as an active ingredient in vaginal contraceptive formulations where it was erroneously thought to be spermicidal when in actuality it inactivates an achrosomal proteolytic enzyme hyaluronidase essential for sperms to penetrate to the ovum. For the last 25 years 3-amino-4-hydroxybenzoic acid has also been in use along with other compounds such as tartaric acid, citric acid, sodium bicarbonate and sodium carbonate as a spermicidal foaming tablet. The foam from the tablet blocks the entrance to the cervix for the sperms, making fertilization difficult. The bubbles create surface tension forces which immobilize sperms so that they do not reach the ovum for fertilization. The soluble sodium carbonate reacts with calcium ions in semen to form the insoluble calcium carbonate (chalk) which arrests sperm (as though they were swimming in mud) and also blocks the entrance to the uterus so that the sperms cannot reach the ovum for fertilization. Should sperms find their way to the ovum they fail to penetrate the coating of the ovum called zona pellucida because, the 3-amino-4-hydroxybenzoic acid inactivates the proteolytic enzyme necessary for digesting the way through the zona pellucida.

The present invention provides use of 3-amino-4-hydroxybenzoic acid or a derivative thereof in the manufacture of a medicament for the prevention or treatment of retrovirus infection. Most preferably the retrovirus is a HTLV, even more preferably HIV. The active ingredient according to the invention covers all aspects of a drug, as a substance other than food, for use to prevent, ameliorate, treat or cure disease, in particular disease caused by retroviral infection.

The most advantageous administration of the active ingredient 3-amino-4-hydroxybenzoic acid is 3 to 10 mg/kg. The most advantageous timing for administration is approximately every 8 to 12 hours. The best results are achieved when this course of administration is continued for at least 28 days.

Furthermore, the present invention provides a method for the prevention or treatment of retrovirus infection comprising the administration of 3-amino-4-hydroxybenzoic acid in a pharmaceutically acceptable carrier. The retrovirus may be HIV.

The active ingredient 3-amino-4-hydroxybenzoic acid or a derivative thereof may be used in combination with one or more of vitamin $B_{12}$ (cyano-cobalamin), folic acid (pteroylglutamic acid) or vitamin C (ascorbic acid) for the prevention or treatment of a retroviral infection presenting with 1 or more opportunistic infections. The active ingredient 3-amino-4-hydroxybenzoic acid is suitable for use against retroviral infection, in particular HIV wherein a patient presents without opportunistic infection. In combination with one or more of vitamin $B_{12}$, folic acid or vitamin C, preferably all three, 3-amino-4-hydroxybenzoic acid is suitable for the prevention or treatment of a retroviral infection (preferably HIV) which presents with one or more opportunistic infections. Additional adjuvant active ingredients and/or adjuvant drugs may be given to patients presenting with opportunistic infections such as T.B., P.C.P., cryptococcal meningitis, dysentery etc.

The present invention also provides a pharmaceutical composition for oral or injectable administration which comprises 3-amino-4-hydroxybenzoic acid or a derivative thereof in combination with a pharmaceutically acceptable carrier, together with any of vitamin $B_{12}$, folic acid, vitamin C or a combination of two or more thereof. Preferably, the 3-amino-4-hydroxybenzoic acid is present in a pharmaceutical composition in an amount of from 25 to 200 mg, more preferably in an amount of 25, 50, 100 or 200 mg. These doses are appropriate for the most effective concentration for treatment of retroviral disease, particularly HIV.

Preferably the composition includes vitamin $B_{12}$, folic acid and vitamin C. The parabens or esters of parahydroxybenzoic acid are known as having bacteriostatic properties. The chemical structure of 3-amino-4-hydroxybenzoic acid is parahydroxybenzoic acid with an additional amino group at C-3. Thus 3-amino-4-hydroxybenzoic acid or a derivative thereof also has bacteriostatic effect. This effect is useful in the treatment of additional opportunistic bacterial infections, preferably in combination with one or more of vitamin $B_{12}$, folic acid and vitamin C.

Preferably the pharmaceutical composition comprises 3-amino-4-hydroxybenzoic acid in combination with up to 20 mcg of vitamin $B_{12}$, up to 10 mg of folic acid and up to 50 mg of vitamin C. Even more preferably the composition comprises 25, 50, 100 or 200 mcg of 3-amino-4-hydroxybenzoic acid in combination with 10 mcg of vitamin $B_{12}$, 5 mg of folic acid and 25 mg of vitamin C.

For a preferred administration of the composition it is in the form of a sugar coated tablet. The formulation of the sugar coated tablet and the method of manufacture thereof are all well known in the art.

The invention is described with reference to the drawings of which:

FIG. 1 is a graph of the decline in the $CD_4$ cell count of AIDS patients over time, and FIG. 2 is a bar graph of the results from Example 4.

The Therapeutic Index of 3-amino-4-hydroxybenzoic acid has been determined. International pharmacological principles demand that for human safety the Therapeutic Index of any drug to be used for human treatment should be greater than a unit, i.e. 1. If the Index is greater than 1, patients can take the drug without medical supervision and without experiencing adverse effects. There are, however, cases where therapeutic indices are less than 1 where the benefits outweigh the risks. This holds in the administration of anti-cancer drugs which mandate the availability of competent medical supervision. The reason behind this is that the drugs are supposed to destroy cancerous human cells. The difference between normal human cells and cancerous human cells is, as expected, minimal. It is expected that the difference between HIV and normal human cells would be colossal. This is suggested as a reason why the Therapeutic Index and safety margin of 3-amino-4-hydroxybenzoic acid is so great.

Therapeutic Index for 3-amino-4-hydroxybenzoic acid is:

$$I = \frac{\text{Lethal dose }(LD50)}{\text{Effective dose }(ED50)}$$

$$= \frac{200{,}000 \text{ mg}}{1} \div \frac{0.5}{1}$$

$$= \frac{200{,}000 \text{ mg}}{1} \times \frac{1}{0.5 \text{ mg}}$$

$$= 400{,}000$$

The index for 3-amino-4-hydroxybenzoic acid is 40,000 which is good mathematical proof to back the safety of 3-amino-4-hydroxybenzoic acid as a drug to treat HIV.

Our experience in using 3-amino-4-hydroxybenzoic acid to treat HIV/AIDS has shown only one non-uniform adverse effect. This is nausea and vomiting in the very weak, which in itself is not a major adverse effect to justify failure to use the highly useful remedy. Septrin causes a similar effect. In the case of 3-amino-4-hydroxybenzoic acid, this occasional side effect can be averted by feeding before administration, giving a flavouring agent before administration or preparing the medicament in capsule form. The nausea is temporary. The medicament is preferably taken for approximately 28 days.

From data on the minimum inhibitory concentration of 0.5 mg/l and the therapeutic index of 40,000 it has been possible to work out an optimum dose of 3–10 mg/kg every eight hours. Higher doses may be given with impunity where there are other problems like nausea and vomiting.

The antimicrobial activity of 3-amino-4-hydroxybenzoic acid has been established in Herpes simplex, in HIV, in bacteria (*Neisseria gonorrhoeae, Treponema pallidum, Escherchia coli*), fungi, *Candida albicans* and the protozoan *Trichomona vapinalis*. This wide anti-microbial activity suggests a mechanism of action which applies for all these microbes.

It is believed that the active ingredient of this invention works by inhibiting protein synthesis at a level not affecting human metabolism. The structure resembles the basic structure of sulfonamides. It could therefore be that 3-amino-4-hydroxybenzoic acid exerts competitive protein synthesis inhibition on these microbes.

The structure resembles that of a thymine analogue and it could also possibly act by being incorporated into the DNA and mRNA at some point to cause misreading of protein synthesis instruction and thereby leading to the formation of non-functional entities and therefore the death of the microbes.

Dipping HIV into aqueous 3-amino-4-hydroxybenzoic acid for only 30 seconds renders the virus uninfective. This duration is too short to be an inhibition of protein synthesis. It could only be an irreversible binding of the viral coat at gp120, gp160 or gp41 thereby making the virus fail to attach itself to the $CD_4$ surface markers of target cells. In this case attachment, adhesion, penetration, replication and inhibition of host cell biochemistry does not occur and the virus dies, remains in the body (harmless) or gets excreted and the host remains fairly healthy. It may also inactivate the lytic enzyme essential for HIV entry into the host cell as it does for hyaluronidase.

When a patient, with a frankly discharging gonorrhoeae was given 1.6 g of 3-amino-4-hydroxybenzoic acid orally, the discharge ceased in 12 hours but recurred in the 24th hour after treatment. This established that 3-amino-4-hydroxybenzoic acid is bacteriostatic and is sufficiently absorbed from the gut.

The fact that the discharge recurred after 24 hours shows that there was sufficient 3-amino-4-hydroxybenzoic acid in the blood by the twelfth hour but excretion reduces the serum concentration to ineffective levels.

This shows that 3-amino-4-hydroxybenzoic acid is well absorbed and excreted and would offer adequate serum levels when given at a frequency of 8 hourly or 12 hourly.

EXAMPLES

Example 1

Safety Studies on Chicken, Rabbit and Sheep

A chicken of 500 g was used and 3-amino-4-hydroxybenzoic acid in water was forced down the esophagus using a plastic syringe over 9 days.

Six rabbits weighing 1.5 kg were given 3-amino-4-hydroxybenzoic acid in injection water intraperitoneally (since they failed to drink), over 9 days.

A 15 kg sheep was given 3-amino-4-hydroxybenzoic acid dissolved in water daily using a 60 cc bottle to push it through the mouth. On the 10th day 3-amino-4-hydroxybenzoic acid was dissolved in injection water to be given I.V. (after sedating the sheep with 20 mg diazepam 1M). It proved difficult so a total bolus of 800 mg of 3-amino-4-hydroxybenzoic acid was given intraperitoneally.

The following table shows 3-amino-4-hydroxybenzoic acid given to the chicken orally, to the 6 rabbits intraperitoneally and to the sheep orally and intraperitoneally over 9 days in gradually increasing doses.

| | WEIGHT (mg/kg body weight) | | | | | | | | |
|---|---|---|---|---|---|---|---|---|---|
| DAY | 1 | 2 | 3 | 4 | 5 | 6 | 7 | 8 | 9 |
| Chicken | 1.56 | 3.12 | 6.26 | 12.52 | 25.0 | 50.1 | 100.2 | 200.3 | 400.6 |
| Rabbit | 0.5 | 1.04 | 2.09 | 4.17 | 8.3 | 16.7 | 33.33 | 66.67 | 133.3 |
| Sheep | 0.05 | 0.10 | 0.21 | 0.42 | 0.83 | 1.67 | 3.33 | 6.67 | 13.3 |

Then the sheep was given a single dose of 800 mg of 3-amino-4-hydroxybenzoic intraperitoneally (53.33 mg/kg).

There were no adverse effects observed from these animal experiments. If 3-amino-4-hydroxybenzoic acid was dangerous it would most likely have shown detrimental effects in the intraperitoneal administration which reached 133.3 mg/kg in the rabbit and 53.3 mg/kg in the sheep. It should be noted that the recommended clinical dose is 3–10 mg/kg per day.

| | Safety Study on Human Volunteers | | |
|---|---|---|---|
| Person | | Dose & Frequency of 3-amino-4-hydroxybenzoic acid Intake | Total 3-amino-4-hydroxybenzoic acid mg/kg |
| 1 | 70 Kg | 200 mg stat | 3 |
| 1 | 70 Kg | 200 mg tds × 2/52 | 120 |
| 2 | 70 Kg | 800 mg stat | 11 |
| 3 | 40 Kg | 800 mg stat | 20 |
| 4 | 70 Kg | 200 mg tds × 5/7 | 43 |
| 5 | 70 Kg | 200 mg tds × 5/7 | 43 |

-continued

Safety Study on Human Volunteers

| Person | | Dose & Frequency of 3-amino-4-hydroxybenzoic acid Intake | Total 3-amino-4-hydroxybenzoic acid mg/kg |
|---|---|---|---|
| 6 | 70 Kg | 200 mg tds × 5/7 | 43 |
| 7 | 70 Kg | 200 mg tds × 5/7 | 43 |

Each person took 3-amino-4-hydroxybenzoic acid orally. Only persons 1 and 3 experienced nausea without vomiting.

Example 3

Clinical observations on HIV/AIDS Patients Treated with 3-amino-4-hydroxybenzoic acid Treatment was administered orally to each patient taking 200 mg of 3-amino-4-hydroxybenzoic acid tds for 14 days.

(1) B.N. was a 30 year old teacher whose wife died in April 1991 of AIDS. He presented with general weakness, weight loss, easy fatigability on exertion, recurrent tonsillitis, mouth ulcers, cervical lymphadenopathy, itchy skin rash and pain in swallowing food. His weight rose from 44–48 kg and haemoglobin rose from 11.69% to 16% after treatment. Lymphocytes rose relatively from 39% to 49%. His signs and symptoms were over by six months of treatment. Follow-up one and half years later showed that he had not lost a single working day because of the sickness.

(2) L.W. was a nurse married with one child. Her illness started as night sweats, weight loss, enlargement of neck lymph nodes, mouth ulcers, pain in swallowing food, mental confusion and general weakness. She was bed ridden at Hospital, unable to go to the bathroom and toilet (dependent on a bed pan). She was transferred to Thika Nursing Home on 31.12.92 on a stretcher and started on 3-amino-4-hydroxybenzoic acid. Within 5 days she was able to go to the toilet and bathroom unaided. She became mentally clear, the oral ulcers, genital wounds and lymph node enlargement were over by the second week of treatment. She gained weight from 41 kg–43.5 kg, i.e. 2.5 kg in 3 weeks and was able to go to the surgery by public taxi alone.

(3) J.K. had general weakness, oral ulcers, pain in swallowing food, diarrhea and loss of appetite. After 2 weeks he had gained 5 kg and the signs and symptoms were over.

(4) W.K. gained 2 kg in 2 weeks.

(5) J.M. gained 1 kg in 2 weeks of treatment.

(6) P.K. had hyper pigmented rashes which used to bleed on scratching. The rashes subsided and the pigmentation returned to normal skin colour in 2 weeks of treatment. She gained 2 kg in 2 weeks.

(7) N.N. was so sick on starting treatment that she could not even be weighed since she could not stand. She was sleeping on the floor unable to climb a two foot bed. In 5 days of treatment she was able to do her house work, go for salary from her place of work and even go to the market for shopping.

(8) B.N. gained weight from 44 kg to 53 kg and haemoglobin from 12.1 to 14.9% in 6 months of treatment.

(9) F.K. a 49 year-old man who was diagnosed seropositive 7 years before he reported for treatment on 27.7.94 made the most impressive progress.

When he came he had anorexia, oral ulcers, straight thin silk hair, vomiting, wasting, diarrhea and anal ulcers. He also had three 2 cm wounds on the right medial side of the ankle and two others over the left medial malleolus which had defied treatment for seven months. He had edema of the legs and a swollen left ankle. He could not stand or walk and was brought supported by two men by the armpits.

After 24 hours of treatment, the diarrhoea ceased. By the third day he could stand and walk unaided. The vomiting and diarrhoea were over by the third day. By end of the second week the recalcitract wounds had healed and all his signs and symptoms were over.

Most interesting is that he had received his viaticum (the last sacrament for the sick and dying) before he started 3-amino-4-hydroxybenzoic acid treatment. He returned to work as a cashier in a busy hotel on 1.9.94. He was in perfect health on 22.1.95 when the Doctor visited him and is still healthy by May 19th 1995 i.e. nine months since treatment which takes only two weeks.

His condition and progress have offered the following very important observations for HIV/AIDS work:

(a) While on average a patient treated with 3-amino-4-hydroxybenzoic acid gains 5 kg within the first month this one had gained only 1 kg in six months of very dramatic improvement.

(b) By the sixth month his haemoglobin rose only by 11.9%–10.99%=1 g % whereas one would have expected a greater improvement. All along the time of treatment, the serum iron was normal.

(c) He was investigated and found to be diabetic which is most likely the reason he failed to gain weight.

(d) His mature onset diabetes has been intermittent.

(e) Other HIV/AIDS patients have been found diabetic which could mean that there is a relationship between HIV/AIDS and diabetes.

(f) By 6 weeks of treatment his thin silk hair had reverted to the normal Afro type. When asked he answered that prior to treatment he did not need to comb it but then, after 6 weeks of treatment, he found the need to comb it.

(g) On examining the blood picture, a medical professor questioned as to whether the patient was taking AZT. He confirmed that he had taken several courses of AZT. It is an established fact that AZT causes bone marrow depression and anaemia in presence of normal serum iron.

(10) L.N. the wife of patient No 9 gained 8 kg in two weeks of treatment with 3-amino-4-hydroxybenzoic acid until she had to buy new dresses.

Example 4

T-Cell Observations after HIV/AIDS Treatment with 3-amino-4-hydroxybenzoic acid

SUMMARY

Symptomatic and asymptomatic seropositive individuals were treated with 3-amino-4-hydroxybenzoic acid (200 mg tds orally) for two weeks. $CD_4$:$CD_8$ ratios were taken before and three months after treatment. It was found that the $CD_4$:$CD_8$ ratio rose and $CD_8$ decreased to varying levels in all of the individuals indicating immunological improvement. Based on its inherent ability to inactivate HIV in vitro it is probable that 3-amino-4-hydroxybenzoic acid suppresses or inactivates the HIV in affected individuals.

INTRODUCTION 3-amino-4-hydroxybenzoic acid has been shown to inactivate HIV cultivated in human lymphocytes at a minimum concentration of 0.5 mg/l without any adverse effect to the lymphocytes. Safety studies as described in Examples 1 and 2 have been done on chicken, rabbit, sheep and human volunteers and proved safe. Only tolerable nausea and occasional vomiting have been noted as side effects. About 20 patients have been treated and assessed clinically, haematologically and by weight gain and found to improve. Those with complications were given adjuvant medication where necessary.

In the attempt to establish whether 3-amino-4-hydroxybenzoic acid has anti-HIV effects the patients were treated and assessed by observing changes in T-cells. With the background knowledge that 3-amino-4-hydroxybenzoic acid has the ability to completely inactivate cultivated HIV it was expected that it would confer some suppression on HIV infection which could be measured quantitatively by changes in T-cells.

MATERIALS AND METHODS

The individuals were taken randomly as they became available (3 male and 4 female). Their T-cell counts were taken before treatment and three months after treatment. They were given 3-amino-4-hydroxybenzoic acid as 200 mg tds orally and followed on daily basis as they took 3-amino-4-hydroxybenzoic acid for two weeks. Thereafter they were followed weekly for the first month after finishing the course of medicine and then monthly.

RESULTS

| Patient No. | Patient Reference | Increase in $CD_4$ after treatment $CD_4/mm^3$ |
|---|---|---|
| 1. | JC004 | 531 |
| 2. | JE006 | 72 |
| 3. | JE007 | 160 |
| 4. | JE009 | 40 |
| 5. | JE0010 | 184 |
| 6. | JE0011 | 102 |
| 7. | JE0012 | 465 |

The results are shown graphically in FIG. 2. The mean increase in $CD_4$ was 208. The reported equivalent increase for the drug AZT is 81.

$CD_4/mm^3$ Changes After Treatment

| Patient Reference | Count Before Treatment | Count After Treatment |
|---|---|---|
| JC004 | 561 | 1092 |
| JE006 | 50 | 112 |
| JE007 | 650 | 810 |
| JE009 | 460 | 500 |
| JE0010 | 300 | 484 |
| JE0011 | 1122 | 1326 |
| JE0012 | 1014 | 1479 |

$CD_4/CD_8$ Ratio Changes Before and After Treatment

| Patient | Before Treatment | After Treatment |
|---|---|---|
| JC004 | 0.845 | 1.632 |
| JE006 | 0.00 | 0.06 |
| JE007 | 0.7 | 2.2 |
| JE009 | 0.3 | 0.2 |
| JE0010 | 0.29 | 0.564 |
| JE0011 | 0.7 | 0.78 |
| JE0012 | 0.9 | 1.11 |

$CD_8$ Changes with Treatment

| Patient | Before Treatment | After Treatment |
|---|---|---|
| JC004 | 39% | 22.3% |
| JE006 | 81% | 31.2% |
| JE007 | 42% | 12.7% |
| JE009 | 65% | 68% |
| JE0010 | 47% | 39% |
| JE0011 |  | 50% |
| JE0012 | 43% | 38% |

These results show there is immunological improvement. Thus 3-amino-4-hydroxybenzoic acid satisfies at least one of the requirements of an anti-HIV drug.

Example 5

Some Important Observations on the Use of 3-amino-4-hydroxybenzoic acid as a Pharmaceutical Agent Against HIV These were made on patients JE001–JE0015 who received 200 mg of 3-amino-4-hydroxybenzoic acid orally only once per day for two weeks and whose T-cell counts were analysed after only 6 weeks.

(1) The results were poor as compared to earlier results on patient reference JC004 who received 200 mg tds for two weeks suggesting the dose might need to be given not less than 3x/day and for a longer duration. Continuous study of viral load by quantitative PCR when available will show the optimum dose and duration of administration of 3-amino-4-hydroxybenzoic acid.

(2) When $CD_4$ cells are counted earlier than three months they tend to show low figures even lower than before the start of treatment. An explanation is that the $CD_4$ cells which carry HIV die after 3-amino-4-hydroxybenzoic acid kills the virus in them. Later as the precursor cells form other $CD_4$s without HIV to destroy them, the total $CD_4$ count will be found even higher than before treatment.

In addition, trial based on clinical and haematological findings have shown the following observations.

(a) Average weight gain is 5 kg within the first month of treatment.

(b) Bed ridden patients can stand and do light work within 2 weeks of treatment.

(c) Anorexia subsides within 5 days.

(d) Diarrhoea stops within 1–3 of treatment.

(e) Fever and weakness subside within 1 week of treatment.

(f) Vomiting ceases within 2 days.

(g) Rashes and hyper pigmentation of scars subside within 5 days.
(i) Haemoglobin normalizes within 1 month.
(j) Sleep normalizes in intensity and rhythm within 2 days.
(k) Oral and anogenital ulcers heal within 1 week.
(l) Poor vision normalizes within 1 week.

Example 6

Blood samples were taken for electron microscopy and HIV culture before and after treatment of two patients. Electron microscopy showed HIV particles before treatment but not 28 days after treatment. Culture taken before treatment grew HIV but not after 28 days of treatment with 3-amino-4-hydroxybenzoic acid.

This shows that 3-amino-4-hydroxybenzoic acid eradicates HIV from the patients blood if administered at a dose of 3 mg/kg tds for 28 days. It therefore qualifies as an anti-HIV drug.

What is claimed is:

1. A method for the treatment of a retrovirus infection comprising the step of administering an effective amount of 3-amino-4-hydroxybenzoic acid or a derivative thereof.

2. The method of claim 1, wherein the retrovirus is HIV.

3. The method of claim 1, wherein the 3-amino-4-hydroxybenzoic acid or derivative thereof is administered at a dosage of from 3 to 10 mg/kg for about every 12 hours.

4. The method of claim 3, wherein the administration is continued for approximately 28 days.

5. The method of claim 1, wherein the 3-amino-4-hydroxybenzoic acid is administered orally or by injection.

6. A pharmaceutical composition comprising:
   (a) 3-amino-4-hydroxybenzoic acid or derivative thereof;
   (b) a pharmaceutically acceptable carrier; and
   (c) an additive selected from the group consisting of vitamin $B_{12}$, folic acid, vitamin C, or a mixture thereof.

7. The pharmaceutical composition of claim 6 comprising from 25 to 200 mg of (a) 3-amino-4-hydroxybenzoic acid or derivative thereof.

8. The pharmaceutical composition according to claim 6 in the form of a sugar coated tablet.

9. The pharmaceutical composition according to claim 6, wherein the upper limit of vitamin $B_{12}$ is 20 mcg, the upper limit of folic acid is 10 mg and the upper limit of vitamin C is 50 mg.

* * * * *